(12) United States Patent
Polikarpus et al.

(10) Patent No.: US 6,984,298 B2
(45) Date of Patent: Jan. 10, 2006

(54) GAS SENSOR HAVING AN INSULATING LAYER

(75) Inventors: Kaius K. Polikarpus, Grand Blanc, MI (US); Walter T. Symons, Grand Blanc, MI (US); Kerry Gross, New Lothrop, MI (US); William J. LaBarge, Bay City, MI (US); Suresh Baskaran, Kennewick, WA (US); Craig Fredrick Habeger, Chillicothe, IL (US); John David Vienna, West Richland, WA (US); Jarrod Vincent Crum, Pasco, WA (US); John Gerard Darab, Doylestown, PA (US); Timothy R. Armstrong, Clinton, TN (US)

(73) Assignee: Delphi Technologies, Inc., Troy, MI (US)

( * ) Notice: Subject to any disclaimer, the term of this patent is extended or adjusted under 35 U.S.C. 154(b) by 251 days.

(21) Appl. No.: 10/042,867

(22) Filed: Jan. 9, 2002

(65) Prior Publication Data

US 2003/0127326 A1 Jul. 10, 2003

(51) Int. Cl.
*G01N 27/407* (2006.01)

(52) U.S. Cl. .................. 204/424; 204/426; 73/23.32
(58) Field of Classification Search ............... 204/424, 204/425, 426, 427, 428, 429; 73/23.31, 23.32
See application file for complete search history.

(56) References Cited

U.S. PATENT DOCUMENTS

| | | | |
|---|---|---|---|
| 4,221,650 A | * | 9/1980 | Friese et al. ............... 204/429 |
| 4,291,107 A | | 9/1981 | Barry et al. |
| 4,298,388 A | | 11/1981 | Sack |
| 5,236,569 A | | 8/1993 | Murase et al. |
| 5,670,032 A | * | 9/1997 | Friese et al. ............... 204/424 |
| 5,676,811 A | * | 10/1997 | Makino et al. ............. 204/425 |
| 5,690,800 A | * | 11/1997 | Friese et al. ............... 204/424 |
| 5,976,335 A | | 11/1999 | Kato et al. |
| 6,350,357 B1 | * | 2/2002 | Wiedenmann et al. ...... 204/426 |
| 6,358,383 B2 | | 3/2002 | Nelson et al. |

FOREIGN PATENT DOCUMENTS

GB   2 294 330 A   4/1996

OTHER PUBLICATIONS

Aldrich Handbook or Fine Chemicals and Laboratory Equipment, 2003–2004.*
T.R. Armstrong & K.D. Meinhardt, "Insulating Substrates For Planar Sensors and Method of Manufacture", Mar., 1999, 3 pages.

* cited by examiner

*Primary Examiner*—Kaj K. Olsen
(74) *Attorney, Agent, or Firm*—Jimmy L. Funke

(57) ABSTRACT

Disclosed herein is a ceramic part, gas sensor, and method for making the gas sensor. The ceramic part comprises: an insulating layer affixed to a substrate wherein the insulating layer comprising $Al_2O_3$ particles; and a glass comprising about 45 to about 69 mole percent $SiO_2$, 0 to about 9 mole percent $B_2O_3$, 0 to about 26 mole percent $Al_2O_3$, 0 and 25 mole percent SrO, and about 10 to about 26 mole percent $RE_2O_3$, where $RE_2O_3$ is selected from the group consisting of $Y_2O_3$, three valent rare earth oxides, and combinations comprising at least one of the foregoing.

In one embodiment of a ceramic part, a gas sensor comprises: an electrolyte layer having disposed on opposite sides thereof a first electrode and a second electrode; and an insulating layer that is in intimate contact with the second electrode, wherein the insulating layer comprises alumina and frit.

The method of making the gas sensor comprises: disposing a first electrode and a second electrode on opposite sides of an electrolyte layer; forming an insulating layer comprising alumina and frit; disposing the insulating layer adjacent to the second electrode to form a green sensor; and heating the green sensor to a temperature sufficient to sinter the electrolyte layer and the insulating layer.

21 Claims, 1 Drawing Sheet

GAS SENSOR HAVING AN INSULATING LAYER

STATEMENT AS TO GOVERNMENT RIGHTS

This invention was made with government support under Contract Nos. AES64633, AES68278, AES73397, and AES73891. The government has certain rights in this invention.

TECHNICAL FIELD

The present disclosure relates generally to ceramic parts and methods for manufacturing ceramic parts. More specifically, the present disclosure relates to an improved electrically insulated layer formed as integral to a ceramic part which itself may be integral to an oxygen sensor.

BACKGROUND OF THE INVENTION

Gas sensors are used in a variety of applications that require qualitative and quantitative analysis of gases. For example, gas sensors have been used for many years in automotive vehicles to sense the presence of oxygen in exhaust gases, such as when an exhaust gas content switches from rich to lean or lean to rich. In automotive applications, the direct relationship between oxygen concentration in the exhaust gas and air-to-fuel ratio of the fuel mixture supplied to the engine allows the gas sensor to provide oxygen concentration measurements for determination of optimum combustion conditions, maximization of fuel economy, and the management of exhaust emissions.

A conventional stoichiometric gas sensor typically consists of an ionically conductive solid electrolyte material, a porous platinum electrode with a porous protective overcoat on the sensor's exterior, which is exposed to the exhaust gases, and a porous electrode on the sensor's interior surface exposed to a known oxygen partial pressure. These electrochemical devices need to be heated to a minimum temperature about 250° C. to 300° C. before they become active, so are usually designed to include an electrically powered heater rather than rely solely on heat from exhaust gas.

Sensors typically used in automotive applications use an yttria-stabilized, zirconia-based electrochemical galvanic cell operating in potentiometric mode to detect the relative amounts of oxygen present in an automobile engine's exhaust. When opposite surfaces of this galvanic cell are exposed to different oxygen partial pressures, an electromotive force is developed between the electrodes on the opposite surfaces of the zirconia electrolyte, according to the Nernst equation:

$$E = \left(\frac{RT}{4F}\right) \ln\left(\frac{P_{O_2}^{ref}}{P_{O_2}}\right)$$

where:
E=electromotive force
R=universal gas constant
F=Faraday constant
T=absolute temperature of the gas
$P_{O_2}^{ref}$=oxygen partial pressure of the reference gas
$P_{O_2}$=oxygen partial pressure of the temperature of the exhaust gas Due to the large difference in oxygen partial pressures between fuel rich and fuel lean exhaust conditions, the electromotive force changes sharply at the stoichiometric point, giving rise to the characteristic switching behavior of these sensors. Consequently, these potentiometric gas sensors indicate qualitatively whether the engine is operating fuel rich or fuel lean, without quantifying the actual air to fuel ratio of the exhaust mixture. Increased demand for improved fuel economy and emissions control has necessitated the development of gas sensors capable of quantifying the exhaust oxygen partial pressure over a wide range of air fuel mixtures in both fuel-rich and fuel-lean conditions. These sensors may have multiple cells, one or more of which is operated amperometrically in conjunction with a gas diffusion barrier to generate a diffusion limited output. The oxygen reference gas may be obtained via an air channel built into the sensor element, and/or pumped electrochemically through the electrolyte from the exhaust gas. Additionally, faster light-off time for the sensor (time to activity) is important for emissions control, as emissions are at the highest levels at startup. Devices with integral heaters have been developed to decrease light-off time.

Gas sensors with a pumped oxygen reference need a stable current to pump oxygen from the exhaust to the oxygen reference. The output of the active zirconia is dependent on having a consistent current of oxygen pumped into the oxygen reference (greater than 7 microamps). Too high a current level caused by a high voltage on the zirconia will cause the output to shift and higher levels will permanently damage the zirconia. A very low current level will cause the zirconia output to shift in the other direction and a sufficiently low current level may allow contamination of the oxygen reference causing a drastic shift in output. The voltage to drive this pumping current may be diverted from a heater through a pumping resistor, or it may be provided by a voltage source in an electronic controller. However, if the resistivity of the alumina body is too low, the leakage current can exceed the current through the pumping resistor. Also, excessive leakage current from the heater can add noise to the sensor signal and contribute to erroneous sensor output.

There exists a need in the art for a higher resistivity tape to reduce electrical leakage during sensor operation.

SUMMARY OF THE INVENTION

Disclosed herein is a gas sensor, method for making the same, and a ceramic part. The gas sensor comprises: an electrolyte layer having disposed on opposite sides thereof a first electrode and a second electrode; and an insulating layer that is in intimate contact with the second electrode, wherein the insulating layer comprises alumina and frit.

The method of making the gas sensor comprises: disposing a first electrode and a second electrode on opposite sides of an electrolyte layer; forming an insulating layer comprising alumina and frit; disposing the insulating layer adjacent to the second electrode to form a green sensor; and heating the green sensor to a temperature sufficient to sinter the electrolyte layer and the insulating layer.

The ceramic part comprises: an insulating layer affixed to a substrate wherein the insulating layer comprising $Al_2O_3$ particles; and a glass comprising about 35 to about 70 mole percent $SiO_2$, 0 to about 30 mole percent $B_2O_3$, 0 to about 26 mole percent $Al_2O_3$, 0 and 25 mole percent $Y_2O_3$, and about 10 to about 26 mole percent $RE_2O_3$, wherein $RE_2O_3$ is selected from the group consisting of $La_2O_3$, three valent rare earth oxides, and combinations comprising at least one of the foregoing.

The above discussed and other features will be appreciated and understood by those skilled in the art from the following detailed description and drawings.

BRIEF DESCRIPTION OF THE DRAWINGS

Referring now to the following FIGURE, that is meant to be exemplary, not limiting, and in which:

The FIGURE is an exploded view of one embodiment of a gas sensor element.

DESCRIPTION OF THE INVENTION

Figure 1:
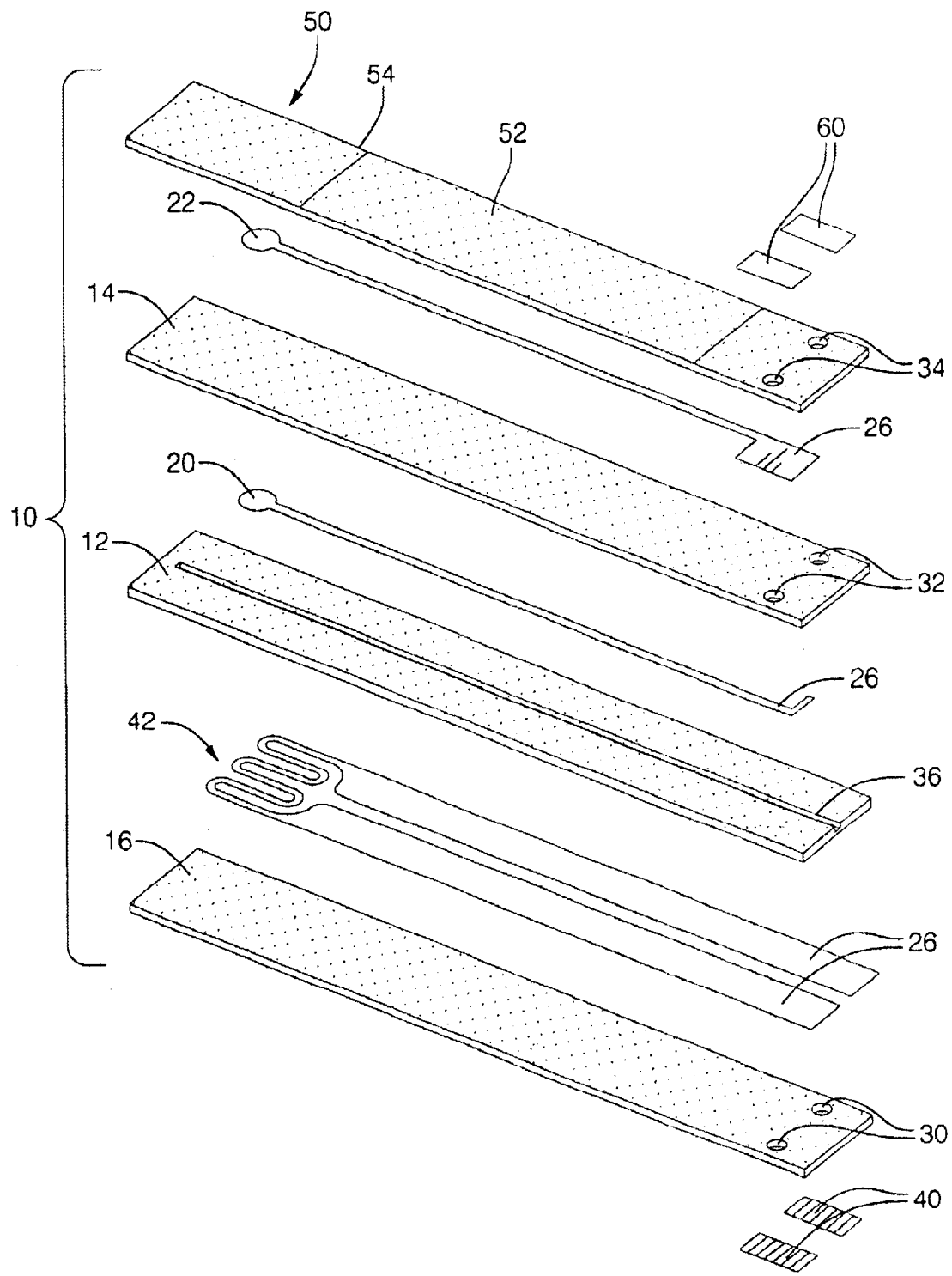

Disclosed is a ceramic part having an insulating layer affixed thereto and a method of manufacturing the same. Ceramics parts should be broadly construed to include devices or components that could contain combinations of ceramic, semiconducting, and/or metallic materials or substrate, including, but not limited to oxygen sensors and microelectronic devices. While the ceramic parts find their greatest utility as components in oxygen sensors, they should be broadly construed to include the method of manufacture and the ceramic parts formed thereby in any use or application. The ceramic part preferably has an electrically insulating layer affixed to a substrate formed as integral thereto. In one embodiment, the ceramic part comprises an insulating layer affixed to a solid electrolyte substrate with the insulating layer formed from a mixture of alumina ($Al_2O_3$) particles and a frit of composition comprising equal to or greater than about 35 mole percent (mol %) silica ($SiO_2$), 0 to about 30 mole percent $B_2O_3$, 0 to about 26 mole percent $Al_2O_3$, 0 to about 25 mole percent $Y_2O_3$, and 0 mol % to about 26 mol % $RE_2O_3$, wherein $RE_2O_3$ is $La_2O_3$, three valent rare earth oxides, or combinations comprising at least one of the foregoing. Preferably, the frit has a thermal expansion coefficient ("CTE") of about $60 \times 10^{-7}$ $K^{-1}$ to about $102 \times 10^{-7}$ $K^{-1}$. It is more preferred to have a frit composition comprising about 35 to about 70 mol % silica, about 20 mol % to about 25 mol % alumina, about 2 mol % to about 8 mol % yttria, about 20 mol % to about 25 mol % lanthana, 0.5 mol % to about 10 mol % boria, and about 10 mol % to about 26 mol % $RE_2O_3$. Especially preferred is a composition comprising about 4 mol % to about 13 mol % boria, 12 mol % to about 27 mol % alumina, about 3 mol % to about 13 mol % yttria, and 0 mol % to about 20 mol % scandia.

Referring to the FIGURE, an example gas sensor 10 is shown. For this arrangement, the sensor comprises an insulating layer, tape, body, or strip 12 disposed in contact with an electrolyte layer 14. A reference gas electrode 20 and sensing electrode 22 are printed on opposite sides of the electrolyte layer 14. Protective layer 50 is in contact with the sensing electrode 22. Protective insulating layer 50 has a porous portion 54 and a dense portion 52 with holes 34 which align with contact pads 60. On the opposite side of electrolyte 14 is a heater 42 is disposed in contact with insulating layer 12 and insulating layer 16. Insulating layer 16 also has via holes 30 which align with contact pads 40. Possible sources to provide oxygen to the reference gas electrode 20 include a channel 36, an oxygen chamber (not shown), and/or an oxygen storage material (not shown), which are disposed in fluid communication with reference gas electrode 20.

In operation, the reference electrode 20 is exposed to a reference gas, such as atmospheric air, while the sensing electrode 22 is exposed to a sensing atmosphere, such as automotive exhaust gas. The electromotive force (emf) measured between the two electrodes, due to the galvanic potential, which represents the partial pressure differences between the sensing atmosphere and the reference gas, can be used to determine the concentration of oxygen in the exhaust gas.

The sensor components, namely the electrodes, heater(s), leads 26, and contact pads, as well as other optional components such as lead gettering layers(s) (not shown), ground plane(s) (not shown) can comprise those conventionally used in the art. The electrodes, leads, contact pads, and heaters can comprise materials conventionally employed in the sensors, such as platinum, palladium, rhodium, osmium, iridium, gold, ruthenium, and other metals, metal oxides, and other materials, as well as oxides, alloys, and mixtures comprising at least one of the foregoing materials.

The solid electrolyte layers can comprise any material conventionally employed as sensor electrolytes, including, but not limited to, zirconia which may optionally be stabilized with calcium, barium, yttrium, magnesium, aluminum, lanthanum, cesium, gadolinium, and the like, as well as oxides, alloys, and combinations comprising at least one of the foregoing materials. For example, the electrolyte can be alumina and yttrium stabilized zirconia.

The insulating layers and the protective insulating layers typically comprise a dielectric material such as alumina, alone or in combination with other oxides. Because these sensors are preferably co-fired, the composition (and properties) of the insulating layers and the protective insulating layers are preferably aligned with the composition (and properties) of the electrolyte layers, i.e. firing shrinkages and coefficients of thermal expansion (CTE), to avoid warping and cracking during or after the firing process.

For example, the electrolyte can be stabilized with yttria that lowers the resistance of the zirconia, thereby increasing the sensor output due to their inverse relationship. The "green", or unfired, sensor is formed and then is heated to sinter the zirconia electrolyte layer and alumina insulating layers or tapes, and to laminate the various components. The problem that arises is that zirconia sinters at a lower temperature than alumina (e.g., below 1,500° C. vs. about 1,550° C. or above). Furthermore, if "over-fired", the zirconia grain size will increase which correlates to reliability problems and renders the sensor susceptible to humidity attack at low temperatures.

To alleviate the zirconia body and alumina body sintering mismatch (e.g., to reduce the alumina sintering temperature), minerals such as clays, talc, dolomite, steatite, fluorspar, kaolin, mullite, borax, spodumene, wollastonite, borides, carbides, nitrides, silicides, carbonates, phosphates, borates, silicates, sulfates, and the like, as well as combinations comprising at least one of the foregoing minerals, can be added to the alumina.

Although the above materials assist in reducing sintering mismatch, they can induce glass formation during processing. This glass can establish alkali ion (e.g., sodium, and the like) collection sites that coat grain boundaries, thereby lowering the electrical resistivity of the tape, and/or resulting in electrical cross talk during sensor operation. To counter this effect, frit can be added to the alumina insulating layers. Basically, higher resistivity can be imparted to the alumina tape while reducing the sintering temperature by using low melting, high resistivity frits as the sintering aid. The frits melt at temperatures less than 1,550° C. and aid in the densification of the alumina. Conventionally, the best alkaline or alkaline earth $M^+$ or $M^{+2}$ densified tape has a room temperature fracture strength of approximately 450 megapascals (MPa) and a resistivity of 1 Megaohm·centimeter (MΩ·cm) at 800° C. While the $M^{+3}$ (e.g., lanthanides, such as $Sc^{+3}$ ($Sc_2O_3$), $Y^{+3}$ ($Y_2O_3$), $La^{+3}$ ($La_2O_3$), $B^{+3}$ ($B_2O_3$), and the like), densified tape has a room temperature fracture strength of about 400 MPa and a resistivity of at least 1,500 MΩ·cm at 800° C. Essentially, a fracture strength of about 300 MPa or greater can be obtained using the frit, with about 400 MPa or greater preferred, and about 450 MPa or greater especially preferred, with a resistivity of about 500 MΩ·cm or greater, with a resistivity of about 700 MΩ·cm or greater preferred, about 1,000 or greater MΩ·cm or greater more preferred, and about 1,500 MΩ·cm or greater especially preferred.

The frit can comprise alkaline earth metals used as network intermediates in glass making, and/or rare earths, and the like. Some possible frit materials include: calcium (Ca), magnesium (Mg), strontium (Sr), lanthanum (La), cerium (Ce), praseodymium (Pr), neodymium (Nd), samarium (Sm), europium (Eu), strontium (Sr), gadolinium (Gd), dysprosium (Dy), boron (B), silicon (Si), scandium (Sc), yttrium (Y), aluminum (Al), and the like, as well as oxides, alloys, and combinations comprising at least one of the foregoing frit materials, with the use of $M^{+3}$ cations most preferred. Although these frits preferably form glass upon cooling, it is understood that the frits include materials which meet the above characteristics yet are crystalline upon cooling.

Preferably, the frit comprises at least about 35 mole percent (mol %) silica ($SiO_2$), with about 45 mol % to about 60 mol % silica more preferred. The balance of the frit can comprise a combination of oxides that comprise about 40 mol % to about 55 mole % of the frit: about 15 mol % to about 25 mol % alumina ($Al_2O_3$) and about 15 mol % to about 25 mol % yttria is preferred, with about 1 mol % to about 9 mol % boria ($B_2O_3$), 17 mol % to about 27 mol % alumina, about 1 mol % to about 3 mol % yttria ($Y_2O_3$), and about 17 mol % to about 27 mol % lanthana ($La_2O_3$) more preferred; and about 4 mol % to about 13 mol % boria, 12 mol % to about 27 mol % alumina, about 3 mol % to about 13 mol % yttria, and 0 to about 20 mol % scandia ($Sc_2O_3$) especially preferred.

The glass formulation is preferably designed to be substantially free of ions lead (Pb), phosphorus (P), barium (Ba), calcium (Ca), strontium (Sr), magnesium (Mg), potassium (K), sodium (Na), and lithium (Li). Specifically, the collective concentration of lead (Pb), phosphorus (P), and alkali ions, are preferably less than about 0.25 mol %, with less than about 0.025 mol % more preferred, and about 0 mol % (i.e., immeasurable via current technology) especially preferred.

Starting feed materials used for preparing the frits are those traditionally used in glass manufacturing processes that include, but are not limited to, oxides, carbonates, sulfates, nitrates, hydroxides, and boric acid. For example, the yttrium-lanthanum-rare earth oxide component can be derived from a pure individual feed material (e.g., pure $Y_2O_3$ and $La_2O_3$), or an unpurified feed material containing a variety of ions (e.g., pure $La_2O_3$ and a variety of rare earth ions). Oxide melts are prepared from the feed material and glasses formed using standard laboratory or industrial unit operations.

For example in the formation of an alumina insulating layer, prior to the addition to the alumina, frits are ground into a fine powder with average particle size of, preferably, less than about 2 micrometers. Up to about 10 weight percent (wt %) glass powder (with about 2 wt % to about 8 wt % preferred, and about 4 wt % to about 6 wt % especially preferred), is mixed with alumina in the proper ratios. The mixture is then mixed with: an organic vehicle (such as methyl ethyl ketone, toluene, xylene, ethanol, hexane, ethyl acetate, trichloroethylene, isopropanol, or the like, or a combination comprising at least one of these organic vehicles); a polymeric binder (such as polyvinyl butyral resin (e.g., Butvar B98 commercial available from Solutia Inc.), or the like) and/or a plasticizer (such as a butyl benzyl phthalate (e.g., Santicizer 160 commercially available from Solutia Inc.), dioctyl phthalate, diethylene phthalate, phthalic acid, adipic acid, sebacic acid, butanol, benzyl alcohol, triethylene glycol, polyethylene glycol, alkyl biphenyls, or the like, as well as combinations comprising at least one of the foregoing plasticizers); and/or a dispersant (such as menhaden fish oil or other fish oils, polyethylene oxyethanol, ethoxylates of castor oil, phosphate esters, or the like, as well as combinations comprising at least one of the foregoing dispersants). Alternatively, an aqueous system composed of water and an acrylic emulsion can be used. The liquid mixture is mixed on a ball mill for a sufficient period of time to form a substantially homogenous mixture (e.g., about 4 to about 12 hours) and cast (e.g., onto Mylar, or the like) by tape casting using, for example, a doctor blade. The tapes are air dried and cut. They can then be stacked to form a sensor and laminated. The tapes are sintered to full density at temperatures of about 1,450° C. to about 1,550° C., with temperatures of about 1,500° C. to about 1,515° C. preferred, for up to about 2 hours or so in air. In other words, the addition of glass lowers the temperature that is required for the alumina tape to attain full density.

The preferred embodiment has a glass transition temperature ($T_g$) of about 750° C. to about 860° C., a softening temperature ($T_s$) of less than about 1,050° C., and a coefficient of thermal expansion (CTE) of about $6.0 \times 10^{-6}$/K to about $8.2 \times 10^{-6}$/K. Table 1 provides a summary of glass compositions and associated properties.

TABLE 1

Summary of Glass Compositions

| Sample | Composition (mole) | | | | | | | Tg Calculated | Ts Calculated | CTE (ppm, $K^{-1}$) Calculated | Tg Measured | Ts Measured | CTE (ppm, $K^{-1}$) Measured |
| --- | --- | --- | --- | --- | --- | --- | --- | --- | --- | --- | --- | --- | --- |
| | $SiO_2$ | $B_2O_3$ | $Al_2O_3$ | SrO | $Y_2O_3$ | $Nd_2O_3$ | $La_2O_3$ | | | | | | |
| 1 | 0.60 | — | 0.20 | — | — | — | 0.20 | 829 | 886 | 6.4 | — | 888 | 7.2 |
| 2 | 0.60 | — | 0.10 | 0.10 | 0.05 | — | 0.15 | 837 | 897 | 7.7 | — | 905 | 7.5 |
| 3 | 0.50 | — | 0.20 | 0.10 | 0.05 | — | 0.15 | 836 | 886 | 8.1 | 837 | 883 | 7.6 |
| 4 | 0.69 | — | — | 0.21 | — | — | 0.10 | 801 | 918 | 7.8 | — | — | — |
| 5 | 0.50 | — | 0.16 | 0.12 | 0.16 | — | 0.06 | 849 | 894 | 8.4 | — | — | — |
| 6 | 0.50 | — | 0.17 | 0.11 | — | 0.21 | 0.01 | 850 | 887 | 8.3 | — | — | — |
| 7 | 0.50 | — | 0.23 | 0.05 | 0.05 | — | 0.17 | 837 | 882 | 7.5 | 840 | 888 | 7.2 |
| 8 | 0.50 | — | 0.26 | — | — | — | 0.24 | 831 | 874 | 7.2 | 853 | 876 | 7.0 |
| 9 | 0.46 | 0.09 | 0.24 | — | — | — | 0.21 | 760 | 804 | 6.9 | 760 | 804 | 6.9 |

TABLE 1-continued

Summary of Glass Compositions

| | Composition (mole) | | | | | | Tg | Ts | CTE (ppm, K$^{-1}$) | Tg | Ts | CTE (ppm, K$^{-1}$) |
|---|---|---|---|---|---|---|---|---|---|---|---|---|
| Sample | SiO$_2$ | B$_2$O$_3$ | Al$_2$O$_3$ | SrO | Y$_2$O$_3$ | Nd$_2$O$_3$ | La$_2$O$_3$ | Calculated | Calculated | Calculated | Measured | Measured | Measured |
| 10c | 0.48 | 0.04 | 0.25 | — | — | — | 0.23 | — | — | — | — | 845 | 7.0 |
| 11 | 0.50 | — | 0.24 | — | 0.03 | — | 0.24 | 838 | 875 | 7.3 | 843 | 884 | 7.5 |
| 12 | 0.475 | 0.05 | 0.225 | — | 0.02 | — | 0.225 | — | — | — | 792 | 832 | 7.3 |
| 13 | 0.375 | 0.302 | 0.029 | 0.25 | — | — | — | — | — | — | 653 | — | 6.7 |

The compositions are illustrated in, but not limited by, the following examples of an alumina tape.

An alumina tape (16) was created with 95.16 wt. % alumina and 4.84 wt. % frit. The frit was composed of 60 mol % SiO$_2$ (29.7 wt. %), 20 mol % Al$_2$O$_3$ (16.8 wt. %), and 20 mol % La$_2$O$_3$ (53.5 wt. %) as found in Table 1 under Sample 1. A material comprising 475.8 grams aluminum oxide powder, 24.2 grams of frit powder, 120 grams of xylene, 120 grams of ethanol and 7.0 grams of menhaden fish oil (a dispersant and release agent) were added to a high purity aluminum oxide lined ball mill. The material was milled with high density, high purity aluminum oxide ⅛ inch diameter mill balls for 12 hours. Next, 64 grams of ethanol, 64 grams of xylene, 53.1 grams of Butvar B98 and 33 grams of Sanitizer 160 were added and the mixture was milled for an additional 4 hours.

The slip was recovered and vacuum de-aerated at about 25 millimeters of mercury (mm Hg) for 1 to 3 minutes. The milled mixture was tape cast on non-silicone coated Mylar film using a doctor blade to form a flexible polymer tape. The tape was removed from the Mylar and cut into 3×2 inch rectangles. Seven tape layers were laminated into a single monolithic structure 3×2×0.125 inches and several 2×0.125×0.125 inch pieces were machined from the larger structure.

Prior to firing, the "green" pieces were measured with an accuracy of ±0.001 inches. Then the pieces were fired at 1,510° C. for 2 hours and re-measured. The shrinkage was determined from the difference between the length of the green part (unfired) and the same part after firing. The X-Y shrinkage was about 16.1%.

In another experiment, an alumina tape (17) was created with 95.16 wt. % alumina and 4.84 wt. % frit. The frit was composed of 47.5 mol % SiO$_2$, 5 mol % B$_2$O$_3$, 22.5 mol % Al$_2$O$_3$, 2 mol % Y$_2$O$_3$, and 22.5 mol % La$_2$O$_3$ as found in Table 1 under Sample 23b. A material comprising 475.8 grams aluminum oxide powder, 24.2 grams of frit powder, 120 grams of xylene, 120 grams of ethanol and 7.0 grams of menhaden fish oil (a dispersant and release agent) were added to a high purity aluminum oxide lined ball mill. The material was milled with high density, high purity aluminum oxide ⅛ inch diameter mill balls for 12 hours. Next, 64 grams of ethanol, 64 grams of xylene, 53.1 grams of Butvar B98 and 33 grams of Sanitizer 160 were added and the mixture was milled for an additional 4 hours.

The slip was recovered and vacuum de-aerated at about 25 millimeters mercury (mm Hg) for 1 to 3 minutes. The milled mixture was tape cast on non-silicone coated Mylar film using a doctor blade to form a flexible polymer tape. The tape was removed from the Mylar and cut into 3 inch by 2 inch rectangles. Seven tape layers were laminated into a single monolithic structure 3 inches by 2 inches by 0.125 inches and several 2 inch by 0.125 inch by 0.125 inch pieces were machined from the larger structure.

Prior to firing, the "green" pieces were measured to have a tolerance of within 0.001 inches. Then the pieces were fired to about 1,510° C. for 2 hours and re-measured. The shrinkage was determined from the difference between the length of the green part (unfired) and the same part after firing. The X-Y shrinkage was about 16.4%.

Table 2 illustrates the resistivity results for samples of tapes including the above-referenced examples. To determine the resistivity of the tapes created, a 0.75-inch circle was cut from a lamination of three tape layers. A 0.5-inch circle of pure platinum ink was centered on each tape. The circle was fired to about 1,510° C. for 2 hours. In a ceramic tube furnace, spring loaded platinum rods were pressed against each platinum face of the platinum coated circle. The furnace was heated to about 800° C. and the resistance between the electrodes measured.

(Note, Sample 14 comprises 100% alumina, no frit, and Sample 15 comprises 95.16 wt % alumina and 4.84 wt % frit (Sample 10 frit)). Values of resistivity for conventional tapes are under 30 MΩ·cm, while a few exhibit values at around 500 MΩ·cm. However, the tapes created, 16 and 17, exhibited a resistivity of 778 MΩ·cm and 1.862 MΩ·cm, respectively. Since a pure alumina tape, without glasses, has a resistivity of about 2,000 MΩ·cm (14), the results for 16 and 17 are desirable with the benefit of structural integrity and better sintering compatibility with yttria stabilized zirconia.

TABLE 2

Resistivity Measurements of Alumina Tape Samples

| Sample | Test Temperature (° C.) | Thickness Average (inches) | Electrode Diameter (inches) | Average Resistance at 10 V (ohms) | DC Volume Resistivity (MΩ · cm) |
|---|---|---|---|---|---|
| 14 | 800 | 0.0197 | 0.4980 | 86,404,440.0 | 2,166.2 |
| 15 | 800 | 0.0198 | 0.6259 | 13,932,429.4 | 551.3 |
| 16 | 800 | 0.0172 | 0.6325 | 16,781,819.6 | 778.5 |
| 17 | 800 | 0.0185 | 0.6288 | 43,691,001.6 | 1,862.5 |

Conventional sensors, when co-firing the alumina tape and zirconia electrolyte, experience a reduced resistivity of the alumina tape. In contrast, employing the frit into the alumina tape increases the resistivity of the alumina tape, the alumina tape may be co-fired with the zirconia electrolyte without affecting the resistivity of the alumina tape, and the compatibility between the alumina tape and the zirconia is improved due to the reduced alumina sintering temperature (about 1,510° C. or less).

The ceramic part can be utilized in applications where one desired component is nonconductive. For example, as a seal between two or more electrically conductive layers, or wherein the glass is utilized as a insulating covering over a conducting metal, such as a platinum strip formed on the surface of the solid electrolyte. In the latter application, particular utility is found in applications where the ceramic part is an oxygen sensor.

While preferred embodiments have been shown and described, various modifications and substitutions may be made thereto without departing from the spirit and scope of the invention. Accordingly, it is to be understood that the present invention has been described by way of illustration only, and such illustrations and embodiments as have been disclosed herein are not to be construed as limiting to the claims.

What is claimed is:

1. A gas sensor, comprising:
   an electrolyte layer having disposed on opposite sides thereof a first electrode and a second electrode; and
   an insulating layer that is in intimate contact with the second electrode, wherein the insulating layer comprises alumina and frit;
   wherein the frit comprises about 35 mol % to about 70 mol % silica, 0 mol % to about 30 mol % boria, 0 mol % to about 26 mol % alumina, 0 to about 25 mol % yttria, 0 to about 26 mol % $RE_2O_3$ where $RE_2O_3$ is $La_2O_3$, three valent rare earth oxides, or combinations comprising at least one of the foregoing $RE_2O_3$s.

2. The gas sensor as in claim 1, further comprising a heater disposed adjacent to the insulating layer.

3. The gas sensor as in claim 1, further comprising a protective insulating layer disposed adjacent to the first electrode.

4. The gas sensor of claim 1, wherein the frit comprises a material selected from the group consisting of alkaline earth metals and rare earths, and oxides, alloys, and combinations comprising at least one of the foregoing materials.

5. The gas sensor of claim 1, wherein the insulating layer comprises up to about 10 wt % frit.

6. The gas sensor of claim 5, wherein the insulating layer comprises about 2 wt % to about 8 wt % frit.

7. The gas sensor of claim 6, wherein the insulating layer comprises about 4 wt % to about 6 wt % frit.

8. The gas sensor of claim 1, wherein the insulating layer has a resistivity of about 700 MΩ·cm or greater at about 800° C.

9. The gas sensor of claim 8, wherein the insulating layer has a resistivity of about 1,000 MΩ·cm or greater at about 800° C.

10. The gas sensor of claim 9, wherein the insulating layer has a resistivity of about 1,500 MΩ·cm or greater at about 800° C.

11. The gas sensor of claim 1, wherein the frit comprises a material selected from the group consisting of lanthanum, cerium, praseodymium, neodymium, samarium, europium, gadolinium, dysprosium, boron, silicon, scandium, yttrium, aluminum, and oxides, alloys, and combinations comprising at least one of the foregoing materials.

12. The gas sensor of claim 1, wherein the frit comprises about 20 mol % to about 25 mol % alumina, about 2 mol % to about 8 mol % yttria, about 20 mol % to about 25 mol % lanthana, and 0.5 mol % to about 10 mol % boria.

13. The gas sensor of claim 1, wherein the frit comprises about 4 mol % to about 13 mol % boria, 12 mol % to about 27 mol % alumina, about 3 mol % to about 13 mol % yttria, and 0 mol % to about 20 mol % scandia.

14. The gas sensor of claim 1, wherein the frit comprises less than about 0.25 mol %, based upon the total mol % of the frit, of elements selected from the group consisting of lead, phosphorus, barium, calcium, magnesium, strontium, lithium, sodium, potassium, and combinations comprising at least one of the foregoing elements.

15. The gas sensor of claim 14, wherein the frit comprises less than about 0.025 mol % of the elements.

16. A gas sensor, comprising:
   an electrolyte layer having disposed on opposite sides thereof a first electrode and a second electrode; and
   an insulating layer disposed adjacent the second electrode, on a side of the second electrode opposite the electrolyte, wherein the insulating layer comprises alumina and frit;
   wherein the frit comprises greater than or equal to about 35 mol % silica, 0 mol % to about 30 mol % boria, 0 mol % to about 26 mol % alumina, 0 to about 25 mol % yttria, 0 to about 26 mol % $RE_2O_3$ where $RE_2O_3$ is $La_2O_3$, three valent rare earth oxides, or combinations comprising at least one of the foregoing $RE_2O_3$s.

17. The gas sensor of claim 16, wherein the frit comprises about 45 mol % to about 60 mol % silica.

18. The gas sensor of claim 17, wherein the frit further comprises about 15 mol % to about 25 mol % alumina and about 15 mol % to about 25 mol % yttria.

19. The gas sensor of claim 17, wherein the frit further comprises about 1 mol % to about 9 mol % boria, 17 mol % to about 27 mol % alumina, about 1 mol % to about 3 mol % yttria, and about 17 mol % to about 27 mol % lanthana.

20. The gas sensor of claim 17, wherein the frit further comprises about 4 mol % to about 13 mol % boria, 12 mol % to about 27 mol % alumina, about 3 mol % to about 13 mol % yttria, and 0 to about 20 mol % scandia.

21. The gas sensor of claim 17, wherein the frit has a thermal expansion coefficient of about $60 \times 10^{-7} K^{-1}$ to about $102 \times 10^{-7} K^{-1}$.

* * * * *